May 20, 1952 G. MERRILL Plant Pat. 1,097

PEACH TREE

Filed Oct. 27, 1950

WITNESS

Addison E. Avery

INVENTOR

Grant Merrill

Webster & Webster

ATTYS.

Patented May 20, 1952

Plant Pat. 1,097

UNITED STATES PATENT OFFICE 1,097

PEACH TREE

Grant Merrill, Red Bluff, Calif.

Application October 27, 1950, Serial No. 192,551

1 Claim. (Cl. 47—62)

This invention relates to a new and distinct variety of yellow-fleshed, freestone peach whose prime characteristic is a very late season harvest, ripening approximately seven to eight weeks later than the J. H. Hale, and one to two weeks later than the Kirkman Gem (United States Plant Patent No. 506).

This late harvest is quite advantageous from the standpoint of fruit marketing, especially where the fruit is highly colored and of tasty flesh, as in the present instance.

The herein described variety of peach tree was originated as a seedling of the Kirkman Gem grown in my breeding plot on my farm near Red Bluff, California.

Seed of the Kirkman Gem was planted in such plot during February 1943, and the parent tree of the instant variety fruited, and was observed to be of novel character, in October 1945.

Subsequently the variety has been successfully reproduced by budding onto seedlings in test plots at Newcastle, California, and Modesto, California, together with cleft grafting onto mature Golden Jubilee trees in my orchard near Red Bluff, California. These reproductions carry forward all of the distinctive characteristics of the parent tree and its fruit.

As compared to the J. H. Hale, the present variety is a larger tree and bears fruit which ripens seven to eight weeks later, but is of comparable market quality, being further characterized by its ability to better withstand cold storage.

As compared to the Kirkman Gem, the tree of the present variety is more vigorous and larger, and bears fruit which ripens one to two weeks later; such fruit being more highly colored, and being more suited to long distant shipment, on account of lack of the soft stripe along the suture, which characterizes the Kirkman Gem.

A further feature of distinction is that the fruit of the present variety is sweeter than that of the Kirkman Gem, or the Late Kirkman (United States Plant Patent No. 920).

Figure 1:
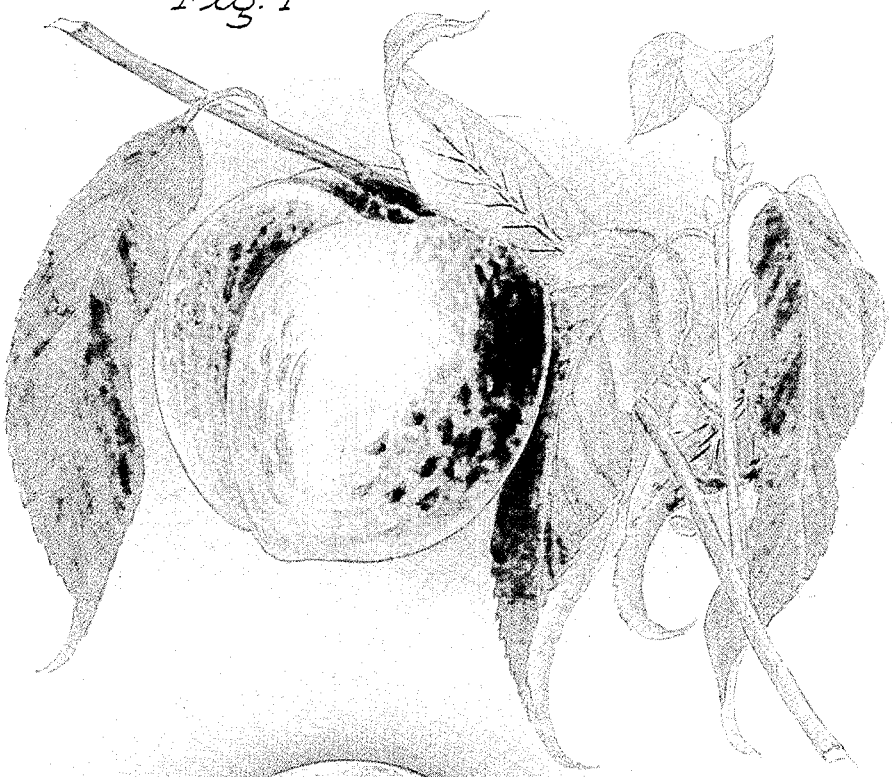
Fig. 1 is a perspective view of one of the fruit as attached to a stem with leaves.
Figure 2:
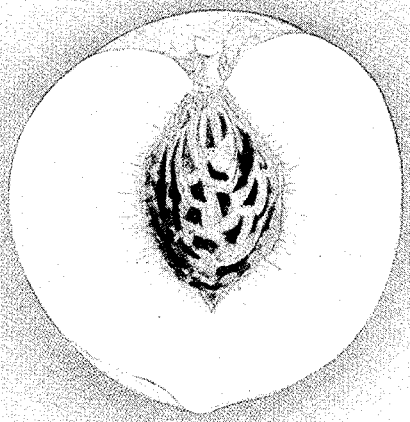
Fig. 2 is a sectional view axially of the fruit, with the stone exposed.

Referring now more specifically to the pomological details of the new and distinct variety of peach tree, the following is an outline description thereof; all major color plate identifications being by reference to Maerz and Paul Dictionary of Color.

Tree: Medium size; medium vigorous; medium upright; medium open; vase formed; productive; regular bearer.

Trunk: Stocky; medium shaggy.

Branches: Medium stocky; medium shaggy; grey-brown. *Lenticels*—medium quantity; medium large.

Leaves: Medium small. Length—4″ to 6½″, average 5½″; width—1″ to 2″, average 1½″. Acuminate; lanceolate; acutely pointed; medium thick; smooth. Color—medium green (23–L–3) on top, with a shading of yellow; lighter green (22–J–4) on the under side.

*Stem twigs.*—Brown (7–L–11).

*Margin.*—Finely crenate to serrate.

*Petiole.*—Medium long; medium slender.

*Glands.*—Number of variable, mostly three to nine. Alternate; medium size; reniform. Green to yellow, mostly on leaves, some on petiole.

*Stipules.*—On new growth—dropping off early.

Flower buds: Medium size; medium length; obtuse; free; pubescent.

Flowers: Midseason. Date of first bloom—March 9, 1950; date of full bloom—March 22, 1950. Large size; light pink.

Fruit: Maturity when described—eating, ripe. Dates of first and last picking—October 1, 1949 and October 17, 1949, respectively.

*Size.*—Large. Average diameter axially—2⅞″; average transversely in suture plane—2⅞″; average cheek to cheek—3″.

*Form.*—Uniform; symmetrical; globose.

*Suture.*—Distinct; shallow. Extends from base to apex, with slight depression beyond pistil point.

*Ventral surface.*—Rounded very slightly; lipped throughout, either side.

*Cavity.*—Elongated in suture plane, with suture showing on one side. Depth—⅜″ to ⅝″, average ½″; breadth—1″ to 1⅝″, average 1 5/16″. Color—yellow under-color, with variable red blush.

*Base.*—Retuse.

*Apex.*—Short; rounded.

*Pistil point.*—Apical.

Skin: Medium thick; medium tough; tenacious to flesh; slight tendency to crack.

*Color.*—Bright yellow (10–J–7 shading into 11–K–8) under-color, with some red blush (7–L–6+) over almost entire fruit, and additional dark red dapple (up to 7–L–6) over three-fourths of surface of the fruit.

*Down.*—Scant; very short; rolls slightly when rubbed.

Flesh:

*Color.*—Yellow (9-K-6 shading into 9-L-7), flecked with red (6-K-6) outwardly from the pit cavity.

*Surface of pit cavity.*—Red, flecked with white.

*Fibers.*—Pink.

*Amygdalin.*—Scant.

*Juice.*—Moderate; rich.

*Texture.*—Firm.

*Fibers.*—Moderate; fine; tender.

*Ripens.*—Evenly.

*Flavor.*—Slightly acid to sweet; mild; delicate.

*Aroma.*—Distinct.

*Eating quality.*—Good. A well balanced combination of acid, sweet, and aroma.

Stone: Free.

*Fibers.*—Very short. Retains very few short fiber-like threads at base only.

*Size.* — Medium. Average length — $1\frac{5}{16}''$; average breadth — 1''; average thickness—¾."

*Form.*—Obovate; acuminate.

*Base.*—Straight to slightly oblique.

*Hilum.*—Oval.

*Apex.*—Acuminate.

*Sides.*—Mostly equal.

*Surface.*—Irregularly furrowed near base, ridges near base to beyond middle.

*Ridges.*—Rounded toward apex.

*Pits.*—Circular to elongated.

*Ventral edge.*—Thick, without wing.

*Dorsal edge.*—Full; shallow; fairly narrow.

*Ridges.* — Grooved toward base to above center on either side; interrupted.

*Color.*—Dark tan (8-J-8) stained with red to wine color.

*Tendency to split.*—Slight.

Use: Market; local; dessert; culinary; canning; freezing; long distance shipment.

Keeping quality: Good.

Shipping quality: Excellent.

The tree and its fruit herein described may vary in slight detail due to climatic and soil conditions under which the variety may be grown.

Having thus described my invention, I claim:

A new and distinct variety of peach tree, substantially as described and illustrated, bearing yellow-fleshed freestone fruit having a very late ripening period in comparison to the J. H. Hale and Kirkman Gem; such ripening period being seven to eight weeks later and one to two weeks later than said varieties, respectively; as further compared to the J. H. Hale the fruit being equal in market quality but withstands cold storage better; and as further compared to the Kirkman Gem the tree being larger and more vigorous, and the fruit being more highly colored, sweeter, and superior for shipping.

GRANT MERRILL.

REFERENCES CITED

The following references are of record in the file of this patent:

UNITED STATES PATENTS

| Number | Name | Date |
|---|---|---|
| Pl. Pt. 920 | Kirkman | Feb. 7, 1950 |